(12) United States Patent
Thele

(10) Patent No.: US 7,754,303 B1
(45) Date of Patent: Jul. 13, 2010

(54) LABEL ASSEMBLY

(76) Inventor: Richard K. Thele, P.O. Box 1681, Shelton, WA (US) 98584

( * ) Notice: Subject to any disclaimer, the term of this patent is extended or adjusted under 35 U.S.C. 154(b) by 1306 days.

(21) Appl. No.: 11/229,136

(22) Filed: Sep. 19, 2005

(51) Int. Cl.
*B32B 9/00* (2006.01)
*G01D 13/00* (2006.01)
*G01K 1/02* (2006.01)

(52) U.S. Cl. .................... 428/40.1; 428/41.6; 428/42.1; 116/200; 116/216

(58) Field of Classification Search ................ 428/40.1, 428/41.6, 42.1; 116/200, 207, 216
See application file for complete search history.

(56) References Cited

U.S. PATENT DOCUMENTS

| | | | |
|---|---|---|---|
| 4,154,107 A | * | 5/1979 | Giezen et al. ............... 116/207 |
| 4,812,653 A | | 3/1989 | Bhattacharjee |
| 5,182,212 A | | 1/1993 | Jalinski |
| D338,413 S | | 8/1993 | Ciambella |
| 5,602,804 A | | 2/1997 | Haas |
| 5,997,927 A | | 12/1999 | Gics |
| 6,244,208 B1 | | 6/2001 | Qiu et al. |

* cited by examiner

*Primary Examiner*—Patricia L Nordmeyer

(57) ABSTRACT

A label assembly includes a plurality of flexible panels sealed together along their peripheral edges. The plurality of panels includes a bottom layer and a top layer. The top layer is substantially transparent. A thermally reactive material is positioned between the top and bottom panels. The thermally reactive material changes to a color when the thermally reactive material attains a selected temperature. A pressure sensitive adhesive is positioned on a bottom side of bottom layer.

5 Claims, 2 Drawing Sheets

LABEL ASSEMBLY

BACKGROUND OF THE INVENTION

1. Field of the Invention

The present invention relates to label devices and more particularly pertains to a new label device for indicating when the temperature of a food product has risen above freezing.

2. Description of the Prior Art

The use of label devices is known in the prior art. U.S. Pat. No. 5,997,927 describes a device that indicates the temperature of a container to which it is attached. Another type of label device is U.S. Pat. No. 4,812,053 having a middle layer which is time reactive to temperature. Another such device is found in U.S. Pat. No. 6,244,208.

While these devices fulfill their respective, particular objectives and requirements, the need remains for a device for indicating when a frozen food item has thawed at some point before consumption. This will alert a person buying the food item that spoilage might have occurred during a thawing period. Additionally, such a device may be configured to indicate other temperature variations aside from

SUMMARY OF THE INVENTION

The present invention meets the needs presented above by generally comprising a plurality of flexible panels sealed together along their peripheral edges. The plurality of panels includes a bottom layer and a top layer. The top layer is substantially transparent. A thermally reactive material is positioned between the top and bottom panels. The thermally reactive material changes to a color when the thermally reactive material attains a selected temperature. A pressure sensitive adhesive is positioned on a bottom side of bottom layer.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
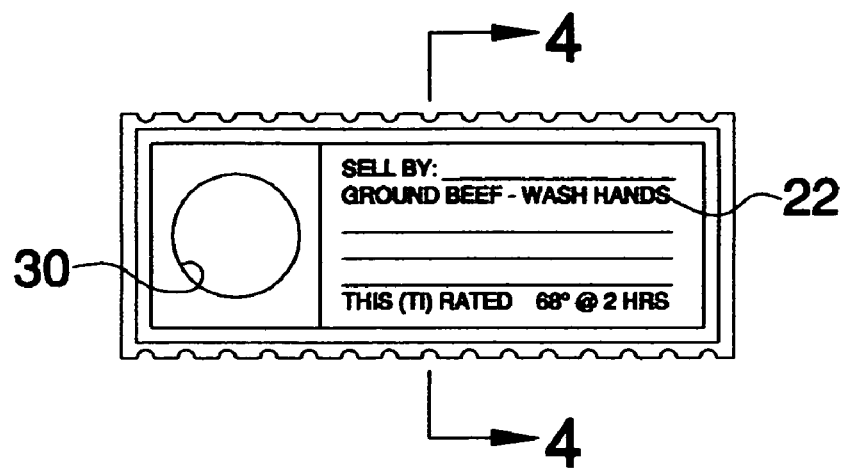
FIG. 1 is a top view of a label assembly according to the present invention.
Figure 2:
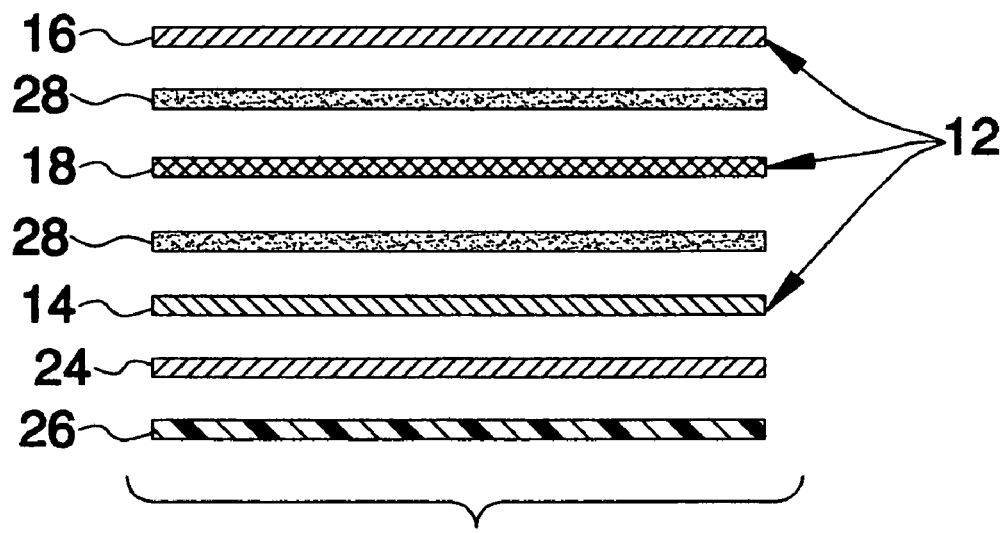
FIG. 2 is an expanded cross-sectional side view of the present invention.
Figure 3:
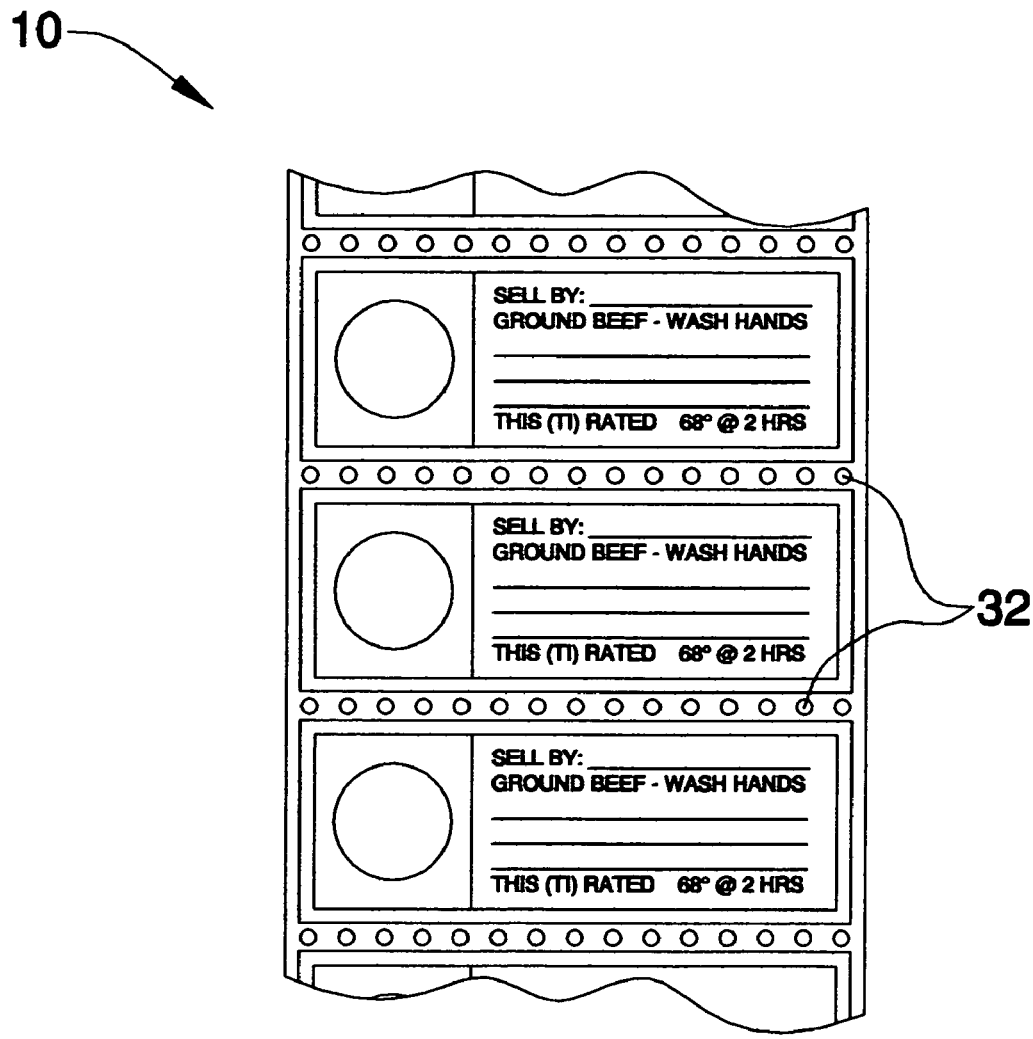
FIG. 3 is a top view of the present invention.
Figure 4:
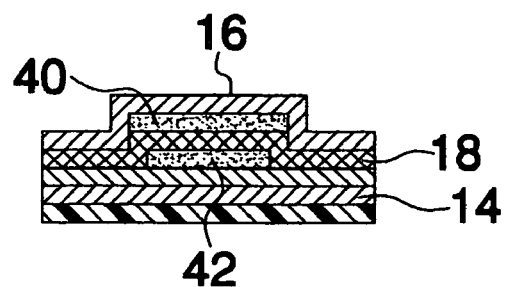
FIG. 4 is a cross-sectional view taken along line 4-4 of FIG. 1.

With reference now to the drawings, and in particular to FIGS. 1 through 3 thereof, a new label device embodying the principles and concepts of the present invention and generally designated by the reference numeral 10 will be described.

As best illustrated in FIGS. 1 through 3, the label assembly 10 generally comprises a plurality of flexible panels 12 sealed together along their peripheral edges. The plurality of panels 12 includes a bottom layer 14 and a top layer 16. The top layer 16 is substantially transparent. The plurality of panels 12 includes a mesh layer 18 positioned between the bottom 14 and top 16 layers. The top 16, bottom 14 and mesh 18 layers are preferably comprised of a plastic material that may be vacuum sealed and then heat sealed along their respective peripheral edges. Label indicia 22 are positioned on the top layer 16. A pressure sensitive adhesive 24 is positioned on a bottom side of bottom layer 14 and a non-stick covering 26 is positioned on and covers the adhesive 24. An opening 30 is formed in the label indicia 22 to see through the top layer 16 if the label indicia covers the top layer 16.

A thermally reactive material 28 is positioned between the top 16 and bottom 14 panels. The thermally reactive material 28 is configured to change to a color when the thermally reactive material attains a temperature greater than zero degrees Celsius, though that temperature may be altered to a selected temperature if the assembly 10 is not being used for ensuring that food has remained frozen. The color is ideally a red color. The thermally reactive material 28 preferably includes two liquid components that become opaque when mixed, and preferably turn a color such as red. The components each preferably have a freezing point generally equal to zero degrees Celsius so that once they melt, the chemicals will mix and change color and the process will be un-reversible. In the present embodiment, the thermally reactive material includes a first component 40 positioned between the mesh layer 18 and the top layer 16 and a second component 42 is positioned between the mesh layer 18 and the bottom layer 14. The first component 40 comprises a clear material and the second component comprises a colored material. The first 40 and second 42 components melt and mix together when the temperature is greater than the zero degree Celsius. The colored material is colored red and the first 40 and second 42 components may comprise water wherein a dye has been added to the second component 42.

In use, the label assemblies 10 are used as conventional labels for frozen food items. Should the food thaw out, the label assembly 10, or more particularly the thermally reactive material 28, will turn a red color to indicate such. The opening 30 is positioned in the label indicia 22 to allow viewing of the thermally reactive material 28. Additional components, having different colors, and additional mesh layers may be added to further indicate the amount of thawing that may have taken place. A plurality of the label assemblies 10 is preferably attached together in strips and separable from each other along perforated lines 32.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A label assembly comprising:
   a plurality of flexible panels sealed together along their peripheral edges, said plurality of panels including a bottom layer and a top layer, said top layer being substantially transparent, said plurality of panels including a fluid permeable mesh layer positioned between said bottom and top layers;
   a thermally reactive material being positioned between said top and bottom panels, said thermally reactive material changing to a color when said thermally reactive material attains a selected temperature, said thermally reactive material including a first component positioned between said mesh layer and said top layer and a second component being positioned between said mesh layer and said bottom layer, wherein said first component comprises a clear material and said second component comprising a colored material, said first and second components melting and mixing together when said temperature is greater than zero degrees Celsius; and
   a pressure sensitive adhesive being positioned on a bottom side of bottom layer.

2. The assembly according to claim 1, wherein said temperature is between zero degrees and one degree above Celsius.

3. The assembly according to claim 1, further including label indicia being positioned on said top layer.

4. The assembly according to claim 1, further including a non-stick covering being positioned on and covering said adhesive.

5. A label assembly comprising:
   a plurality of flexible panels sealed together along their peripheral edges, said plurality of panels including a bottom layer and a top layer, said top layer being substantially transparent, said plurality of panels including a fluid permeable mesh layer positioned between said bottom and top layers, label indicia being positioned on said top layer;
   a thermally reactive material being positioned between said top and bottom panels, said thermally reactive material changing to a color when said thermally reactive material attains a temperature greater than zero degrees Celsius, said thermally reactive material including a first component positioned between said mesh layer and said top layer and a second component being positioned between said mesh layer and said bottom layer, said first component comprising a clear material and said second component comprising a colored material, said first and second components melting and mixing together when said temperature is greater than zero degree Celsius, said colored material being colored red;
   a pressure sensitive adhesive being positioned on a bottom side of bottom layer; and
   a non-stick covering being positioned on and covering said adhesive.

* * * * *